United States Patent [19]
Affeld et al.

[11] Patent Number: 4,559,648
[45] Date of Patent: Dec. 24, 1985

[54] SAFETY CONTROL VALVE FOR AN ARTIFICIAL HEART

[75] Inventors: Klaus Affeld; Axel Mohnhaupt; Frank Jorn, all of Berlin, Fed. Rep. of Germany

[73] Assignee: Thoratec Laboratories Corporation, Berkeley, Calif.

[21] Appl. No.: 625,506

[22] Filed: Jun. 28, 1984

[30] Foreign Application Priority Data

Jun. 29, 1983 [DE] Fed. Rep. of Germany ....... 3323862

[51] Int. Cl.⁴ ................................................ A61F 1/24
[52] U.S. Cl. ............................................ 623/3; 91/28
[58] Field of Search ........................... 3/1.7; 128/1 D; 417/394; 91/28, 510

[56] References Cited

U.S. PATENT DOCUMENTS 2,396,984  8/1944  Broadston et al. .................... 91/28
4,173,796 11/1979  Jarvik ..................................... 3/1.7

OTHER PUBLICATIONS

*The International Journal of Artificial Organs/* vol. 5, No. 3, 1982/ pp. 157–159, "Completely Integrated Wearable TAH–Drive Unit", H. P. Heimes, F. Klasen.

Primary Examiner—Richard J. Apley
Assistant Examiner—James Prizant
Attorney, Agent, or Firm—Flehr, Hohbach, Test, Albritton & Herbert

[57] ABSTRACT

A safety drive for an artificial heart, if the right drive should fail it is simply put out of operation, while if the left drive fails, the right drive, which is still functioning, is switched over to the left circulatory pump and thus serves as a system-internal backup drive.

7 Claims, 3 Drawing Figures

SAFETY CONTROL VALVE FOR AN ARTIFICIAL HEART

The invention concerns a drive with special safety reserves for a pneumatic artificial heart. Pneumatic artificial hearts are usually powered by a drive located outside the body. This drive must be distinguished by especially high operating reliability. In contrast to the case with other artificial organs, such as the artificial kidney, for example, any malfunctioning of the drive for an artificial heart carries with it an immediate risk of death. Besides having components specially selected to reliability, the drive must also have a structure which increases the safety of the system.

Drives for pneumatically driven circulatory pumps are available in which compressed air is modulated by pulse-actuated magnetic valves in such a way that the drives are able to power the pneumatic circulatory pumps. Another existing arrangement is to have this pulsed compressed air generated by reversing pneumatic pistons. In a further variant, reversing rotary compressors are used to generate the pulsed compressed air. Until now, increased safety could be achieved only by a very careful selection of components and by having a backup system available should one of the drives break down. These drives, however, are usually very cumbersome, so that it is barely possible for the patient to move about with even one drive, and with the backup system this becomes extremely difficult. Futhermore, when a drive fails two pneumatic lines must be replaced, entailing additional risk.

The present invention eliminates the problem of the possible lack of a backup system, while at the same time offering much higher system reliability than that of an individual drive. This problem is solved according to the invention in that individual drives are used for both the left and right ventricles; the drives are not coupled to each other either mechanically or electrically, but are interconnected by signal and air flow components in such a way that the drives for the left pump can be replaced by that for the right. This characteristic of the system is based on the practical finding that for a limited time the body is basically dependent only on the power of the pump to the left side and can do without the operation of the right pump for a more or less prolonged period of time. Thus if the right drive breaks down due to a mechanical or electrical failure there is no immediate danger to the patient, and there is ample time available to connect up a new drive. If the left drive fails, on the other hand, in the system according to the invention the right drive is switched over so that it serves as the drive for the left pump.

This switching can be done manually, after the user of the drive is alerted to a malfunction by an alarm, or it can be done automatically. The average pressure in the compressed-air tubing of the left drive can be used as an appropriate signal, this pressure clearly registering above zero when the left drive is functioning. If the left drive fails, then this pressure drops to a much lower value close to the zero point. This pressure drop can be used to make the switch over by means of an installed mechanism. The averaging of the pressure can be performed in a simple manner by a capillary and the switching itself by a spring component, which is held down by the average pressure in the left drive system during normal operation. The switch over should be executed so that the left pump is disconnected from the right drive system and the defective left drive system is also disconnected from the lines to the left pump. It is useful to have the switch designed so that it functions bistably, that is, so that it is stable at the two end positions but unstable in the middle.

In another embodiment this switch over can also be accomplished by an electromechanical servo component, which does the switching based on an analysis of the pressure signals or of drive signals. After the switch over the right drive suddenly has to pump against a high pressure. This sudden assumption of the left pumping load can also be accomplished in an especially simple and reliable manner according to the invention if the drive is regulated to follow a reference volume curve rather than a reference pressure curve. In normal operation the two drives are synchronized with each other by having the left drive follow the left auricular pressure or the left pulmonary arterial pressure. These pressures can be measured either directly or indirectly, or they are determined by means of signals obtained from an analysis of the pneumatic drive pressure of the left pump in the diastolic phase.

The advantages which the invention is intended to offer consist particularly in the fact that the need to have available or carry along a complete backup system is eliminated, and nearly the same level of safety is achieved through a characteristic of the drive according to the invention.

Referring to the drawing.

Figure 1:
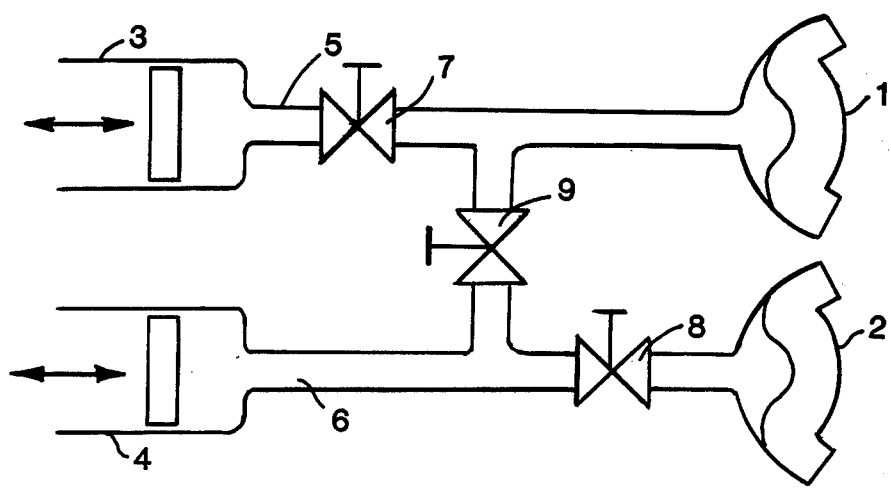
FIG. 1 is a schematic diagram showing one embodiment of the invention.

FIG. 1 shows the left circulatory pump 1 and the right pump 2, which are driven by a drive—here a piston—and 4. The pressure pulse is tansmitted by tubing lines 5 and 6. In normal operation valves 7 and 8 are open, while valve 9 is closed. Should the right drive 4 fail, the left drive 3 is able to take over the entire circulatory load. If the left drive 3 fails, however, it is disconnected from the circulatory pump 1 by the valve 7, and the right drive 4 is disconnected from the right pump 2 by the valve 8 and switched to the left pump 1 by the opening of the valve 9. In this way the right drive 4 takes over the entire circulatory load.

Figure 2:
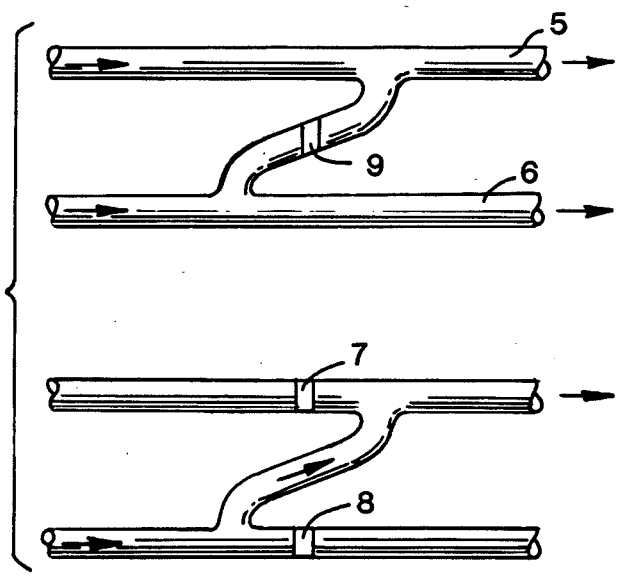
FIG. 2 is a switching diagram showing the operation of the system.

Referring to the switching diagram of FIG. 2, the top portion represents normal operation with lines 5 and 6 free-flowing and valve 9 closed to separate the two systems. The bottom portion shows the condition of the system if there is a malfunction: both pumps are closed off from their original drives by valves 7 and 8, while valve 9 is open.

Figure 3:
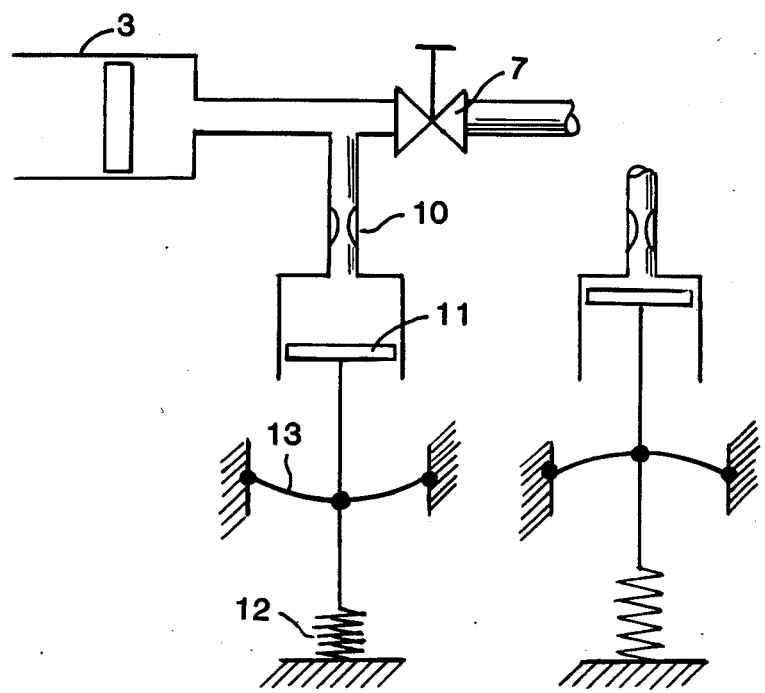
FIG. 3 is a schematic diagram showing an automatic switch for use in accordance with the invention.

Referring to FIG. 3, there is shown an automatic mechanical switch for use with the embodiment of FIG. 1. A branch with a capillary 10 is provided between left drive 3 and the valve 7. As long as drive 3 is able to function, a pulsed pressure prevails in the system, which is time-averaged by the capillary 10 and when at the time average exerts positive pressure on a piston 11 and thus compresses a spring 12. If drive 3 fails, the pulsed pressure is absent and the spring 12 presses the piston 11 back to the position shown at the right of FIG. 3. This motion of the piston is used to bring about the valve switching, as described above, in the manner according to the invention. Meanwhile a bistable spring element 13 ensures that the valve is able to assume only one of the two positions—normal or disrupted—and prevents it from slipping into a middle position.

What is claimed is:

1. A safety drive for an artificial heart, comprising left and right pneumatic circulatory pumps each made of biocompatible material and each being driven by one of two mutually independent pneumatic drives, and means for switching the drive for said right pneumatic circulatory pump to serve as a backup drive for the left pneumatic circulatory pump.

2. A safety drive according to claim 1, wherein said means for switching is automatic and includes a mechanically bistable switch.

3. A safety drive according to claim 1 wherein said means for switching is manual.

4. A safety drive according to claim 2 wherein said switching means includes an isolated servo component responsive to an analysis of a compressed air signal from the left pneumatic circulatory pump.

5. A safety drive according to claim 2 wherein the left and right drives are regulated according to an air volume flow reference curve.

6. A safety drive according to claim 2 wherein, in normal operation, the volume flow of the left drive is regulated by the left auricular pressure, and upon failure of the left drive the right drive is also regulated by the left auricular pressure.

7. A safety drive according to claim 2 wherein the left air volume flow is regulated by a signal from an analysis of the pneumatic drive pressure of the left pump in the diastolic phase.

* * * * *